United States Patent [19]

Herman et al.

[11] Patent Number: 5,179,020
[45] Date of Patent: Jan. 12, 1993

[54] ANTIBIOTIC RESISTANT STRAIN OF LACTOBACILLUS ACIDOPHILUS

[75] Inventors: Richard E. Herman, Redmond; Douglas R. Ware, Bothell; Julia E. Clarke, Bellevue, all of Wash.

[73] Assignee: Bio Techniques Laboratories, Inc., Redmond, Wash.

[21] Appl. No.: 746,873

[22] Filed: Aug. 19, 1991

[51] Int. Cl.$^5$ .............................................. C12N 1/20
[52] U.S. Cl. .................................. 435/252.9; 435/854
[58] Field of Search ...................... 435/252.9, 854; 424/93 J

[56] References Cited

U.S. PATENT DOCUMENTS

| | | | |
|---|---|---|---|
| 3,343,962 | 9/1967 | Peer | 99/9 |
| 3,953,609 | 4/1976 | Farr | 426/4 |
| 3,984,575 | 10/1976 | Farr | 426/61 |
| 4,657,762 | 4/1987 | Mikkola et al. | 424/93 |
| 4,689,226 | 8/1987 | Nurmi et al. | 424/93 |
| 4,815,042 | 3/1989 | Pratt | 366/141 |
| 4,839,281 | 6/1989 | Gorbach et al. | 435/34 |
| 4,889,433 | 12/1989 | Pratt | 366/141 |
| 4,946,791 | 8/1990 | Manfredi et al. | 435/252.9 |
| 4,980,164 | 12/1990 | Manfredi et al. | 424/93 |

FOREIGN PATENT DOCUMENTS 1134206 11/1968 United Kingdom .
1167196 10/1969 United Kingdom .

OTHER PUBLICATIONS

Mayra-Makinen et al. J. Appl. Bact. 55: 241-245, 1983.
Kleeman, E. G. et al. J. Dairy Sci. 65: 2063-2069, 1982.
Klaenhammer, T. R. J. Dairy Sci. 65: 1339-1349, 1982.
Product Information: Cobactin TM $^{DR}$ Microbial Gastro-Intestinal Stabilizer, Bio Techniques Laboratories, Inc., Redmond Wash.

Primary Examiner—Nathan M. Nutter
Attorney, Agent, or Firm—Christensen, O'Connor, Johnson & Kindness

[57] ABSTRACT

New strains of *L. acidophilus* capable of adhering to the tissue cells of various species of animals and having resistance to both erythromycin and streptomycin are described. The strains may be used in a suitable carrier as a dietary supplement for providing a source of the bacteria in an animal.

1 Claim, No Drawings

ANTIBIOTIC RESISTANT STRAIN OF LACTOBACILLUS ACIDOPHILUS

FIELD OF THE INVENTION

This invention relates to novel microorganisms, particularly to strains of the bacteria *Lactobacillus acidophilus*, which are capable of interspecific attachment to epithelial cells of various animals, and which are capable of growing in the presence of both erythromycin and streptomycin. The invention further relates to food compositions containing these microorganisms and to processes for providing a source of such microorganisms to an animal in the form of dietary supplements.

BACKGROUND OF THE INVENTION

Lactobacillus is a genus of bacteria in the family Lactobacteriacae, which are found in the intestinal tracts of mammals, on green plants, in milk and fermented foods. Lactic acid is produced by these bacteria via carbohydrate fermentation; thus, lactobacilli have been introduced into the manufacture of food products, such as yogurt and cheese, to enhance their quality and stability. In addition, lactobacilli form an important part of the intestinal microbial flora in humans and other animals. In humans, lactobacilli are present in the mouth, lower intestine and vagina.

Other types of bacteria, for example *Escherichia coli* (hereafter *E. coli*), are also present in animals. Pathogenic strains can cause serious intestinal problems such as diarrhea and gastroenteritis. A proper balance of the microbial populations in the intestinal tract of animals is believed to be important to provide resistance to such diseases. Conditions such as stress can alter the balance of microbes in the intestinal tracts of humans and other animals making them more susceptible to disease. This knowledge of the importance of maintaining a proper balance of microorganisms has led to the development of therapy designed to maintain the proper balance. Such therapy has included the use of strains of *L. acidophilus* in dried form, administered orally, for promoting *L. acidophilus* colonization in human intestines. For a review see W. E. Sandine et al. J. Food Protection 42:259-262 (1979). Moreover, *L. acidophilus* has shown some effectiveness in inhibiting *E. coli* in infants suffering from diarrhea.

*L. acidophilus* has also been used in animal feed in an attempt to restore and stabilize the intestinal microbial balance. In some cases, animals such as pigs showed improved growth and exhibited a decreased population of *E. coli* when administered lactobacilli. Two patents (U.S. Pat. No. 3,343,962 and U.K. Pat. No. 1,134,206) disclose methods of preparation of certain lactobacilli for use in animal feed supplements.

Unfortunately, in field studies outside of the laboratory, prior preparations using known strains of Lactobacillus have proven ineffective, in part a) because sufficiently high numbers of viable microorganisms have not been present in the feed preparations and/or b) the organisms were unable to successfully colonize the subject being treated. In such studies it would be desirable to identify and enumerate lactobacilli in feed preparations and intestinal and fecal contents but such laboratory measurements are complicated by the large number of environmental microorganisms commonly encountered in these field samples.

It is thought that adhesion is a primary event in bacterial colonization of a particular habitat, such as the intestinal tract. Bacteria are known to adhere to various surfaces, including human and animal cells; see G. W. Jones, "The Attachment of Bacteria to the Surfaces of Animal Cells," in *Microbial Interactions* (Russing, E.), Chapman and Hall, London (1977), incorporated by reference herein. Attachment appears to be important for establishing and maintaining either the normal- or disease-associated bacterial flora in humans and other animals. For example, bacterial attachment to human mucosal epithelial cells, such as vaginal cells, has been studied and related to possible colonization and invasion by pathogens [R. A. Mardh and L. Westrom, *Infection and Immunity*, 13, p. 661-666(1976); Chan et al., *Infection and Immunity*, 47, pp. 84-89 (1985)].

Differences exist between strains of *Lactobacillus acidophilus* in their ability to survive, initiate and maintain a bacterial population within the intestine due, in part, to differences in the ability of the various strains to adhere to intestinal epithelial cells in different species of animals. These differences may hamper the effectiveness of therapeutically- or prophylactically-administered bacteria. Some lactobacilli strains demonstrate species specificity, such that one strain of *L. acidophilus* from a chicken source will not adhere to ephithelia of a different species, e.g., a rat, as shown by N. Suegara et al., *Infection and Immunity*, 12, p. 173-179 (1975); and R. Fuller, *J. Applied Bact.*, 45, p. 389-395 (1978). The stomach and intestinal tract also present physical challenges to the growth and survival of microorganisms such as Lactobacillus. For example, the mucosal clearance mechanisms of the small intestine wash out any organisms that cannot attach to intestinal epithelial cells or multiply fast enough to avoid dilution. Thus, it would be highly desirable to have strains of Lactobacillus with known species specificity as well as routine laboratory assays for determining the effectiveness of the administered bacteria in an animal host.

It is believed that bacteria may attach to animal cells through a variety of mechanisms. In one system, cations may provide a bridge via ionic attraction between surfaces of the bacteria and epithelial cells. This system appears to be nonspecific and is calcium dependent. In another mechanism, the bacteria appear to attach by contacting receptor sites on the epithelial cells. This system is calcium independent and has been found to be species specific, suggesting that the ability to adhere (i.e., to recognize receptors) when mediated by this mechanism is under the genetic control of the bacteria. At least one researcher has identified two subpopulations of human *L. acidophilus* wherein one population requires calcium to adhere to human fetal epithelial cells and attachment of the other was found to be independent of calcium. One of these strains is capable of interspecific attachment. Such calcium independent attachment has been found in only a few other human bacterial strains [E. G. Kleeman and T. R. Klaenhammer, J. Dairy Sci., 65, pp. 2063-2069 (1982)]. Other mechanisms of bacterial attachment may also be involved, [Sherman et al., *Appl. Environ. Microbiol.*, 52, p. 302-304 (1986); Fuller et al., *Am. J. Clin. Nutr.*, 27, pp. 1305-1312 (1974)].

A commercially available Lactobacillus feed additive concentrate for cattle, containing *L. acidophilus* BT1386 (ATCC No. 53545) and sold under the trademark COBACTIN®, (BioTechniques Laboratories, Inc., Redmond, Wash., addressed many of the above problems. Although BT1386 has been highly successful as a commercial feedlot additive, further improvements in certain characteristics of the strain are desirable. For instance, it is difficult to recover, identify, and enumerate lactobacilli of strain BT1386 in animal feed, tissue, feces, etc., because of the large number of background microorganisms present in these samples. Quantitation of *L. acidophilus* is important to ensure that the microbial inoculum of the feed has been properly prepared and that the animal has been inoculated with a proper dose. Utilizing a marker gene to identify bacteria is routine in the art, e.g., a marker gene conferring the ability to utilize a unique carbon source, however, this method is not widely applicable to samples from an animal, or from bacterium-containing food compositions because of the large numbers of bacteria present in these samples and the diversity of carbon sources utilized by the bacteria in them.

The present invention relates to novel strains of *L. acidophilus* that address the problems of recovery, identification, and enumeration which are described above.

SUMMARY OF THE INVENTION

The present invention provides a new strain of *L. acidophilus* capable of adhering interspecifically to animal cells, and which is relatively easily identified and quantified in samples due to its resistance to antibiotics. In particular, the present invention relates to a strain ATCC No. 55221 (referred to hereafter as BT1389) and related strains that are able to grow in the presence of concentrations of erythromycin and streptomycin which are inhibitory to a majority of other bacteria present in the samples from a treated-animal, or in bacterium-containing food compositions. The ability of BT1389 to survive in the presence of both erythromycin and streptomycin facilitates recovery, quantitation, and identification of this strain of lactobacilli, especially when isolated from samples of animal feed, tissue, intestinal contents or fecal samples.

The present invention also relates to a composition that contains the new strains of *L. acidophilus* in a suitable carrier, such as a sugar carrier for use as a dietary supplement in an animal. The composition may be used to provide a therapeutic, prophylactic, or food source of the new strain of bacteria to an animal.

The invention further relates to methods of treating animals with a microorganism so as to protect the animals from disease, stimulate their growth, promote feed conversion efficiency and the like. The method involves treating the animals with suitable compositions containing the *L. acidophilus* strain of the present invention.

DETAILED DESCRIPTION OF THE INVENTION

The present invention describes biologically pure, novel strains of *L. acidophilus* that are capable of attaching interspecifically to the tissue of animal species, including human, bovine, poultry, and porcine tissue, and which are also capable of growing in the presence of the antibiotics erythromycin and streptomycin. The preferred strain is BT1389 but other strains having the identifying characteristics of BT1389 (illustrative examples of which are detailed below), also fall within the scope of this invention. The novel strains of *L. acidophilus* may be used as a food additive, for example, as a supplement to commercial cattle feed, to provide a source of *L. acidophilus* to the animal. The bacteria may also benefit the animal by improving the efficiency of conversion of food consumed by the animal. The dual antibiotic resistance of the lactobacilli strains is useful in tests for identifying and quantifying the strain in samples from the animal or in bacterium-containing food compositions.

As used herein, the term "animal" refers to animals, e.g. mammals and poultry, kept or raised for use or pleasure including, but not limited to, cows, chickens, pigs, sheep, and the like.

ISOLATION AND SELECTION

The novel strain of *L. acidophilus*, BT1389, was produced using selection and screening procedures described below, starting with the parent strain BT1386 (ATCC No. 53545), which is disclosed in U.S. Pat. Nos. 4,946,791 and 4,980,164 and incorporated herein by reference.

The initial selection for an antibiotic resistant strain was performed by spread plating *L. acidophilus* strain BT1386 onto MRS agar medium containing 600 mg/ml of streptomycin. When approximately $1 \times 10^8$ colony forming units of BT1386 were spread onto this medium, only six were able to grow and form colonies. Since these bacteria were not exposed to a mutagen, their growth indicated that they were streptomycin resistant as the result of spontaneous mutation. One streptomycin resistant mutant was chosen for further studies after partial characterization showed that it had all the desirable characteristics of BT1386, namely, ability to, survive in feed supplements, ferment a wide variety of carbohydrates, attach to epithelial cells in a calcium independent manner, and survive at low pH and in the presence of bile. This mutant was designated strain BT1388. It was found that strain BT1388 improved identification of *L. acidophilus* in livestock feed or fecal samples when isolation was accomplished by culture in Rogosa medium containing streptomycin at 600 mg/ml. However, streptomycin did not satisfactorily reduce the growth of the background environmental microorganisms found in these samples to permit identification or enumeration of BT1388.

In order to further decrease the growth of background microorganisms, while still allowing detection of *L. acidophilus*, a mutant of BT1388 with resistance to a second antibiotic, but while also retaining the desirable commercial properties of BT1386, was obtained by serially transferring BT1388 in MRS broth medium containing increasing concentrations of erythromycin (Em) as outlined below:

1. A fresh overnight culture of BT1388 was transferred in broth containing various concentrations of Em ranging from 0–25 mg/ml. Growth was observed in cultures containing up to 0.5 mg/ml of Em after incubation for three days at 37° C. in 5% $CO_2$. (All subsequent incubations were also done at 37° C. in 5% $CO_2$.)
2. Cells growing at 0.5 mg/ml Em were transferred into fresh broth containing 0.5 or 1.0 mg/ml Em. Growth was observed at up to 1.0 mg/ml Em after overnight incubation.
3. Cells growing at 1.0 mg/ml Em were transferred into fresh broth containing 1.0, 5.0 or 10.0 mg/ml of Em. Growth was observed at up to 5.0 mg/ml Em after overnight incubation.
4. Cells growing at 5.0 mg/ml Em were transferred into fresh broth containing 5, 10, 15 or 20 mg/ml Em. Growth was observed at up to 15 mg/ml Em after overnight incubation.

5. Cells growing at 15 mg/ml Em were transferred into fresh broth containing 150 mg/ml Em. Growth was observed after three days of incubation. A repeated transfer in 150 mg/ml Em resulted in growth after overnight incubation.

Erythromycin at 150 mg/ml, when combined with 600 mg/ml of streptomycin, was shown in other studies to be sufficient to suppress the growth of most environmental contaminants commonly encountered in feed and animal samples, even when collected from a feedlot setting. After growth in medium containing 150 mg/ml Em, a pure culture of resistant *L. acidophilus* was obtained by streak plate purification on MRS agar medium containing 15 mg/ml Em. Colonies were observed after 48 hours of incubation and a single, well isolated colony was selected. This spontaneous erythromycin resistant mutant was designated strain BT1389.

CHARACTERIZATION

Strain BT1389 was partially characterized and found to have all the desirable commercial characteristics of strain BT1386 (as indicated above), and in addition was resistant to streptomycin and erythromycin. Thus, the BT1389 mutant has a genotype allowing expression of the following phenotypes: 1) resistance to erythromycin (e.g., up to a concentration of at least 1.2 mg/ml); 2) resistance to streptomycin (e.g., up to a concentration of at least 5.0 mg/ml); 3) oxygen tolerance sufficient to allow use as a feed supplement; and, 4) ability to promote weight gain and efficiency of feed conversion in animals.

Recovery of *L. acidophilus* strain BT1389 from animal feed, digesta, tissue and feces is facilitated by the ability of the combination of streptomycin and erythromycin to inhibit the growth of background microorganisms. The selective recovery of *L. acidophilus* BT1389 was best practiced by using Rogosa agar medium containing streptomycin (600 mg/ml), erythromycin (150 mg/ml) and miconazole (25 mg/ml). Miconazole was added to inhibit the growth of fungi.

METHODS FOR CULTURE AND STORAGE

Lactobacilli of strain BT1389 can be cultivated by known techniques that involve inoculating a growth medium with a mother culture of the BT1389 lactobacilli. The lactobacilli cells are grown by semi-anaerobic fermentation and harvested by concentrating the fermented medium.

A representative method of concentrating the cells grown up in the fermentation process uses a continuous centrifuge at approximately $9,000 \times g$. Centrifugation is preferably continued until approximately 90 to 95% of the cells are recovered. Other methods of concentrating the cells can be used so long as they provide the desired degree of concentration and do not destroy an excessive number of live cells. The cell concentrate can be collected continuously from the centrifuge. After collection, the cell concentrate should be refrigerated, for example, by placing a vessel carrying the collected concentrate in an ice bath. Depending on the length of time over which the concentrate is collected, the cell concentrate can be collected in one container and periodically transferred to another container sitting in an ice bath.

Once the centrifuging step is complete or a predetermined amount of cell concentrate has been collected, the concentrate is prepared for storage, such as by freezing, lyophilization and the like. Viability may be increased on storage by addition of a suitable cryoprotectant or stabilizing agent (e.g. non-fat milk, inositol, monosodium glutamate, mono- and di-saccharides) to frozen concentrates of the bacterial suspension prior to lyophilization or freezing.

A representative method for freezing the concentrate first adjusts the pH of the concentrate to about 6.4 to 6.5. The pH can be adjusted by adding potassium hydroxide or another basic compound that is not lethal to the bacteria. In this representative embodiment, the cell concentrate is then dispensed into suitable individual containers, for example, metal cans. The concentrate is then frozen as quickly as practicable, for example, using liquid nitrogen or a less expensive alcohol and dry ice bath. Preferably, the mode of freezing should freeze the concentrate within about 10 minutes. After the concentrate is frozen, it can be stored at sub-zero temperatures, for example $-20°$ F. The frozen concentrate does not necessarily include cryoprotectants but such can be added as powders to a collected cell concentrate to be preserved by lyophilization; or, as carrier solids that are added to the lyophilized cell concentrate after lyophilization.

A packaged frozen concentrate typically has a solids-to-live bacteria ratio less than the solids-to-live bacteria ratio of a packaged lyophilized culture. For example, the frozen concentrate may contain about 7.5 grams of solids per 10,000 doses of live bacteria (approximately $5 \times 10^{12}$ colony forming units, CFU) for cattle. The majority of the weight of the frozen concentrate is attributable to water. For example, an amount of frozen concentrate adequate to provide the 10,000 doses of bacteria described above would include approximately 67.5 grams of water. In contrast, a lyophilized culture contains about 100 grams of solids per 10,000 does of live bacteria (approximately $5 \times 10^{12}$ CFU) for cattle.

METHODS FOR ORAL ADMINISTRATION AND FEEDING

As a feed supplement, the frozen concentrate of bacteria can be directly deposited into a volume of the aqueous medium or it can be thawed first and then added to the aqueous medium. For example, about 75 grams of a frozen concentrate of bacteria added to approximately 10 to 25 gallons of water yields a quantity of bacteria in suspension sufficient to dose 10,000 head of cattle at a single feeding. For beef cattle, the concentration of the cells per dose should be at least about $5 \times 10^8$ CFU per dose. For dairy cows, the concentration should be even higher. The amount of feed to which this dosage should be added can be predetermined for an individual animal by measuring daily feed consumption. For poultry, about 75 grams of the frozen concentrate of bacteria added to approximately 7 gallons of water yields a quantity of bacteria in suspension sufficient to dose approximately 1,000,000 head of poultry at a single feeding. Orally acceptable carriers may be added, e.g. sugars (e.g. sucrose, lactose, fructose, maltose); or, proteins (e.g. non-fat milk solids such as casein).

Suitable methods and apparatus to dispense strains of the invention in feed supplements are described in U.S. patent application Ser. No. 07/555,910 (filed Jul. 19, 1990). The apparatus is preferably locatable at a feedlot where batches of the bacterial suspension can be formulated and prepared in advance of dispensing the bacteria into livestock feed or drinking water.

The suspension of the frozen concentrate in an aqueous medium is prepared in accordance with one embodiment as also described in U.S. patent application Ser. No. 07/555,910 (filed Jul. 19, 1990). A satisfactory suspension of the bacteria within the water is evidenced qualitatively by uniform cloudiness of the suspension and a substantial absence of sedimentation. The uniformity of the suspension can also be qualitatively determined by adding a coloring agent such as food coloring and observing the uniformity of the color of the suspension. Quantitatively, the uniformity of the concentration of the bacteria in suspension can be evaluated by removing samples from several levels in the vessel and culturing for live cells of the pure bacterial culture. The respective cultures can be compared to determine the concentration of cells in each of the samples. A uniform suspension should provide samples from different locations in the vessel that have cell concentrations within about 10% to 20% of each other.

Nonuniformity of the concentration of the bacteria in the suspension is undersirable because the doses administered from the suspension to the livestock will have nonuniform bacteria concentrations. In order to ensure that the suspension is uniform, the operator, just prior to dispensing the suspension of bacteria, should observe the suspension for uniform cloudiness or uniform coloring of the suspension.

A commercially available system for delivering the BT1389 bacterial suspension to the livestock or poultry without adding additional feed additives or liquid diluents is sold under the name THE LIQUID SPRAY, by Liquid Systems, Inc., Greenville, S.C. An example of a delivery system capable of measuring, dispensing, and delivering different combinations and proportions of microingredient feed additives concentrates into aliquots of the bacterial suspension is described in U.S. Pat. Nos. 4,815,042 and 4,889,433.

The suspension is preferrably dispensed into the livestock feed just before feeding to the livestock. As the suspension of bacteria is added to the livestock feed, the feed may be tumbled or otherwise agitated to ensure uniform dispersion of the bacteria throughout the feed. Afterward, the feed is delivered to feed bunks for presentation to the animals.

The invention will now be further illustrated by way of the following Examples.

EXAMPLE 1

Identification and Enumeration of *L. acidophilus* Strains of Interest in the Presence of Naturally-Occurring Microorganisms When enumerating *L. acidophilus* in samples of animal feed, tissue and fecal materials, it is common practice to use Rogosa medium since it permits selective growth of lactobacilli and some streptococci. However, it was determined that identification and enumeration of a particular strain of *L. acidophilus* in a feed supplement was very difficult because of the large number of bacteria in the samples, and the difficulty distinguishing the strain of interest from other naturally-occurring (i.e. environmental) lactobacilli. Current practice relies on distinguishing *L. acidophilus* from other background microorganisms by colony morphology. However, this proved not to be reliable because naturally-occurring lactobacilli often had a similar colony morphology to the strain of interest.

When two samples of typical beef feedlot ration were spread plated onto Rogosa medium supplemented with miconazole (25 μg/ml) to inhibit yeast and mold, the average level of background microorganisms in the sample was determined to be $2.4\times10^6$ cfu/gram of ration. Identifying and enumerating an *L. acidophilus* strain of interest was very difficult against this background, especially since *L. acidophilus* is usually introduced into the feed ration at a level of about $5\times10^4$ cfu/gram. Thus, only 2% of the microbial colonies on Rogosa medium would be expected to be the *L. acidophilus* strain of interest.

Operationally, in order to obtain a statistically reliable enumeration of *L. acidophilus* bacterial colonies for determining titer it is desirable for the Rogosa spread plates to contain between 30 to 300 colonies of the strain of interest. When the strain of interest represents only 2% of the total microorganisms that will grow on the plate, the background on the same plate can be calculated to be approximately 1500 to 15,000 colonies. Thus, the identificatiion and enumeration of the strain of interest is very difficult, if not near impossible.

*L. acidophilus* strain BT1388, resistant to streptomycin, was isolated in an attempt to improve identification and enumeration of the strain of interest in the presence of other naturally-occurring lactobacilli. Unfortunately, the background level of microorganisms growing on Rogosa medium containing streptomycin (600 μg/ml) and miconazole (25 μg/ml) was still unacceptably high, as many naturally-occurring organisms were resistant to streptomycin. The large number of colonies growing on these plates causes potential problems contributing to errors in identification and enumeration of the strain of interest: namely, a) crowding of colonies on the plate made it difficult to determine colony morphology (i.e. which colonies were lactobacilli); and, b) the production of metabolic wastes (e.g. lactic acid) by the naturally-occurring microorganisms could potentially be inhibitory to the growth of the strain of interest.

The BT1389 strain was developed in an attempt to overcome problems in identification and enumeration of the *L. acidophilus* strain of interest. When typical feed samples supplemented with *L. acidophilus* strain BT1389 were spread-plated onto Rogosa medium containing miconazole (25 μg/ml), streptomycin (600 μg/ml) and erythromycin (150 μg/ml) the naturally-occurring background microorganisms were completely inhibited and an average of $2.4\times10^4$ cfu/gram of strain BT1389 was easily identified and enumerated. Thus, utilizing *L. acidophilus* strain BT1389 in conjunction with Rogosa medium containing both streptomycin and erythromycin provided identification and enumeration of the strain of interest, even in the presence of a large excess of naturally-occurring microorganisms, in a manner which for the first time allows statistically reliable enumeration of the strain of interest.

EXAMPLE 2

The Effect of Oral Administration and Continuous Feeding of *L. acidophilus* Strain BT1389 in a Bovine Model Two independent field studies were conducted with feedlot cattle. The first trial (Trial I) consisted of 300 animals, and the second trial (Trial II) consisted of 984 animals, see Table 1 (below).

Test Animals

Newly arrived feeder cattle (steers), of various sizes and weights (approximately 405 lbs. each) were divided into a BT1389 or Control group. In Trial I 5 replicates of 30 animals were assigned to the BT1389 group and 5 replicates of 30 animals to the Control group; in Trial II 510 animals in 6 replicates were assigned to the BT1389 group and 474 animals in 6 replicates were assigned to the Control group. The BT1389 group received a feed additive containing a dose of *L. acidophilus* strain BT1389, as described below, and the control group received no bacteria.

Administration of Additive

Vials containing freeze-dried *L. acidophilus* strain BT1389 for use in a solid feed additive were used for preparing oral doses for administration to animals in the BT1389 group. Doses for the BT1389 group consisted of $5 \times 10^8$ colony forming units (CFU) of strain BT 1389 per animal per day in an orally acceptable carrier (i.e. sugar) and doses for the Control group consisted of only the sugar carrier and no bacteria. Using the solid feeding phase, treated feed was prepared on a daily basis by suspending the contents of one vial in one liter of clean water in a clean container and evenly distributing the material over the feed and mixing. The feed was then emptied into the labeled hopper.

To ensure that the cattle took in the full dose of bacteria, the average minimum amount of intake of feed per day, per animal, was predetermined, and the full dose incorporated into that amount of feed. Treated feed left over from the previous day was discarded.

Measurements

Measurements were taken on the initial weight of each individual animal, in pounds, on arrival at the feed lot. Daily feed intake was measured to determine the total feed intake per animal, per day, and this data was recorded by an on line computer for constant processing. Each group of animals was weighed at 28 day intervals after the initial weighing, and a final weight taken after about 133 days in Trial I, and 122 days in Trial II, i.e. at the end of the two studies. Observation of the general health of the animals were made at the start, at weekly, and at the conclusion of the study.

Data Analysis

The one-way statistical analysis of variance technique was used to analyze weight gains, feed intakes, and feed conversion data. Feed conversion is a measure of the amount of feed required for the animal to gain one pound of weight, and may be calculated by dividing intake by weight gain for a given time period. Table 1 below shows the mean feed conversion for the two groups. Statistical significance of the results is indicated by comparing the results obtained at 133 days in Trial I and 122 days in Trial II. The calculated Least Significant Differences (LSD) with the predicted LSD values obtained from the analysis of variance. Feed conversion values which result in a calculated LSD which exceeds the predicted LSD are considered significant.

As can be seen from Table 1 BT1389 improved weight gain and efficiency of feed conversion of animals in the Trial I and II compared to animals in the Control groups. Feed conversion of animals receiving BT1389 were signficantly different from animals in the Control animals at the level of $p < 0.05$.

TABLE 1

| Weight Gain and Feed Conversion in Cattle | | | | |
|---|---|---|---|---|
| | Control | | BT 1389 | |
| | Trial I | Trial II | Trial I | Trial II |
| Average Daily Weight Gain (lbs.) | 2.87 | 3.11 | 2.99 | 3.16 |
| Feed Conversion* | 6.89 | 5.90 | 6.53 | 5.75 |

*Expressed as the mean value for feed conversion per trial group of animals where feed conversion = (lbs. of feed consumed/lbs. of weight gained).

While the preferred embodiments of the invention have been described, it will be appreciated that various changes can be made therein without departing from the spirit and scope of the invention, the scope of which is set forth in the following claims.

The embodiments of the invention in which an exclusive property or privilege is claimed are defined as follows:

1. A substantially pure culture of a strain of *L. acidophilus* having the identifying characteristics of ATCC No. 55221.

* * * * *